(12) United States Patent
Wu et al.

(10) Patent No.: US 8,048,021 B2
(45) Date of Patent: *Nov. 1, 2011

(54) MEDICINAL IMPLANT DEVICE AND CARTRIDGE

(75) Inventors: Zhangwen Wu, New Hope, PA (US); Michael J. Rello, Harleysville, PA (US); James F. Hooper, Jr., Wenonah, NJ (US); James R. Lawter, Yardley, PA (US)

(73) Assignee: Orapharma, Inc., Warminster, PA (US)

( * ) Notice: Subject to any disclaimer, the term of this patent is extended or adjusted under 35 U.S.C. 154(b) by 86 days.

This patent is subject to a terminal disclaimer.

(21) Appl. No.: 12/621,602

(22) Filed: Nov. 19, 2009

(65) Prior Publication Data

US 2010/0136502 A1    Jun. 3, 2010

Related U.S. Application Data

(60) Provisional application No. 61/119,212, filed on Dec. 2, 2008.

(51) Int. Cl.
*A61M 31/00* (2006.01)
*A61C 5/04* (2006.01)

(52) U.S. Cl. .......................... 604/63; 433/89

(58) Field of Classification Search .............. 604/57–64; 433/80, 89, 90
See application file for complete search history.

(56) References Cited

U.S. PATENT DOCUMENTS

| | | | |
|---|---|---|---|
| 1,347,622 A | 7/1920 | Deinnger | |
| 3,625,208 A | 12/1971 | Frost et al. | |
| 3,638,314 A | 2/1972 | Lopez | |
| 3,990,152 A | 11/1976 | Hirdes | |
| 4,079,518 A | 3/1978 | Marshall | |
| 4,092,778 A | 6/1978 | Hirdes | |
| 4,105,030 A | 8/1978 | Kercso | |
| 4,165,800 A | 8/1979 | Doherty et al. | |
| 4,175,326 A | 11/1979 | Goodson | |
| 4,377,380 A | 3/1983 | Vadas et al. | |
| 4,400,170 A | 8/1983 | McNaughton et al. | |
| 4,431,414 A | 2/1984 | Lawrence | |
| 4,479,781 A | 10/1984 | Herold | |
| 4,560,352 A | 12/1985 | Neumeister | |
| 4,581,022 A | 4/1986 | Leonard et al. | |
| 4,641,766 A | 2/1987 | Vlasich | |
| 4,658,993 A | 4/1987 | Vlasich | |

(Continued)

FOREIGN PATENT DOCUMENTS

EP    1489988    12/2004

(Continued)

OTHER PUBLICATIONS

Extended European Search Report dated Nov. 8, 2010 for EP10176527.

(Continued)

*Primary Examiner* — Nicholas Lucchesi
*Assistant Examiner* — Nathan R Price
(74) *Attorney, Agent, or Firm* — Pepper Hamilton LLP

(57) ABSTRACT

The invention includes a device for inserting a medicament within a body cavity of a mammal, and a cartridge for containing the medicament within the device, where the cartridge includes a housing, a retractable chamber for containing medicament disposed within the housing, and a substantially stationary member disposed within the barrel of the retractable chamber, where upon activation of the device, the retractable chamber is retracted about the substantially stationary member, thereby depositing medicament within the body cavity.

12 Claims, 10 Drawing Sheets

U.S. PATENT DOCUMENTS

| | | | |
|---|---|---|---|
| 4,680,027 A | 7/1987 | Parsons et al. |
| 4,693,684 A | 9/1987 | Blatherwick |
| 4,726,769 A | 2/1988 | Hirdes |
| 4,732,302 A | 3/1988 | Muhlbauer |
| 4,768,955 A | 9/1988 | Hirdes |
| 4,784,607 A | 11/1988 | Francois |
| 4,801,263 A | 1/1989 | Clark |
| 4,813,602 A | 3/1989 | Corey |
| 4,813,871 A | 3/1989 | Friedman |
| 4,863,072 A | 9/1989 | Perler |
| 4,871,094 A | 10/1989 | Gall |
| 4,909,788 A | 3/1990 | Egolf |
| 4,993,948 A | 2/1991 | Cameron et al. |
| 4,995,540 A | 2/1991 | Colin |
| 5,000,886 A | 3/1991 | Lawter |
| 5,004,124 A | 4/1991 | Stefaniak et al. |
| 5,112,307 A | 5/1992 | Haber et al. |
| 5,129,825 A | 7/1992 | Discko, Jr. |
| 5,137,181 A | 8/1992 | Keller |
| 5,143,661 A | 9/1992 | Lawter |
| 5,236,355 A | 8/1993 | Brizzolara |
| 5,244,388 A | 9/1993 | Frush |
| 5,250,026 A | 10/1993 | Ehrlich et al. |
| 5,273,532 A | 12/1993 | Niezink et al. |
| 5,286,257 A | 2/1994 | Fischer |
| 5,297,698 A | 3/1994 | Martin |
| 5,306,147 A | 4/1994 | Dragan |
| 5,322,511 A | 6/1994 | Armbruster et al. |
| 5,328,367 A | 7/1994 | Johnson |
| 5,366,733 A | 11/1994 | Brizzolara |
| 5,500,228 A | 3/1996 | Lawter et al. |
| 5,622,498 A | 4/1997 | Brizzolara et al. |
| 5,626,473 A | 5/1997 | Muhlbauer et al. |
| 5,722,829 A | 3/1998 | Wilcox. |
| 5,743,431 A | 4/1998 | Brattesani |
| 5,743,436 A | 4/1998 | Wilcox |
| 5,755,362 A | 5/1998 | Rodriguez, Jr. |
| 5,782,633 A | 7/1998 | Muhlbauer |
| 5,783,205 A | 7/1998 | Berggren et al. |
| 5,800,169 A | 9/1998 | Muhlbauer |
| 5,865,804 A | 2/1999 | Bachynsky |
| 5,871,355 A | 2/1999 | Dragan et al. |
| 5,947,728 A | 9/1999 | Riebl |
| 6,047,864 A | 4/2000 | Winkler |
| 6,083,002 A | 7/2000 | Martin et al. |
| 6,234,795 B1 | 5/2001 | Fischer |
| 6,268,000 B1 | 7/2001 | Romer |
| 6,296,484 B1 | 10/2001 | Nihei |
| RE37,439 E | 11/2001 | Firth et al. |
| 6,319,002 B1 | 11/2001 | Pond |
| 6,334,774 B1 | 1/2002 | Mark |
| 6,494,715 B1 | 12/2002 | Riebl |
| 6,500,001 B2 | 12/2002 | Horth |
| 6,585,696 B2 | 7/2003 | Petersen |
| 6,612,465 B2 | 9/2003 | Pierson |
| 6,648,641 B1 | 11/2003 | Viltro |
| 6,682,348 B2 | 1/2004 | Lawter |
| 6,752,798 B2 | 6/2004 | McWethy |
| 6,802,822 B1 | 10/2004 | Dodge |
| 6,843,652 B2 | 1/2005 | Xie |
| 7,014,462 B1 | 3/2006 | Tilse |
| 7,033,343 B2 | 4/2006 | McWethy et al. |
| 7,198,485 B2 | 4/2007 | Hamman |
| 7,976,489 B2 | 7/2011 | Lawter et al. |
| 7,976,490 B2 | 7/2011 | Lawter et al. |
| 7,976,491 B2 | 7/2011 | Lawter et al. |
| 2003/0186190 A1 | 10/2003 | Lokhandwala |
| 2003/0186191 A1 | 10/2003 | Lawter et al. |
| 2004/0152042 A1 | 8/2004 | Lawter |
| 2004/0225322 A1 | 11/2004 | Garrison et al. |
| 2005/0202365 A1 | 9/2005 | Cao |
| 2007/0027469 A1 | 2/2007 | Smith et al. |
| 2009/0142727 A1 | 6/2009 | Lawter et al. |
| 2009/0142728 A1 | 6/2009 | Lawter et al. |
| 2009/0148500 A1 | 6/2009 | Lawter et al. |

FOREIGN PATENT DOCUMENTS

| | | |
|---|---|---|
| JP | 2002536090 | 10/2002 |
| WO | WO 01/72235 A1 | 10/2001 |
| WO | WO 03/082139 A1 | 10/2003 |
| WO | WO 2009/073700 A1 | 6/2009 |
| WO | WO 2010/065317 A1 | 6/2010 |

OTHER PUBLICATIONS

International Search Report dated Jul. 9, 2003 for PCT/US03/09579.
International Search Report dated Feb. 9, 2009 for PCT/US2008/085364.
International Search Report dated Jan. 26, 2010 for PCT/US2009/065064.

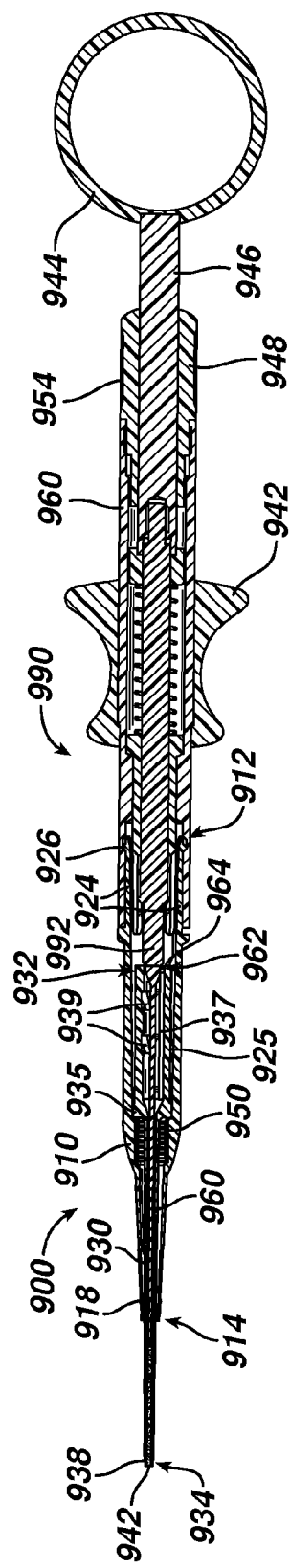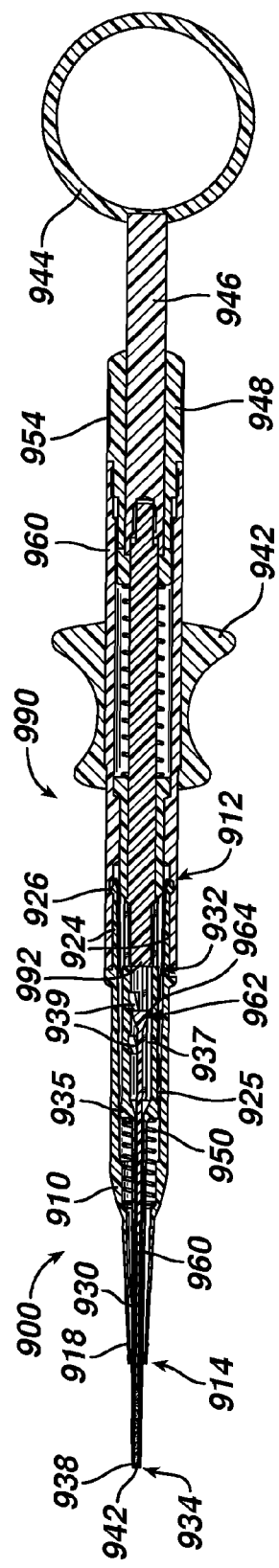

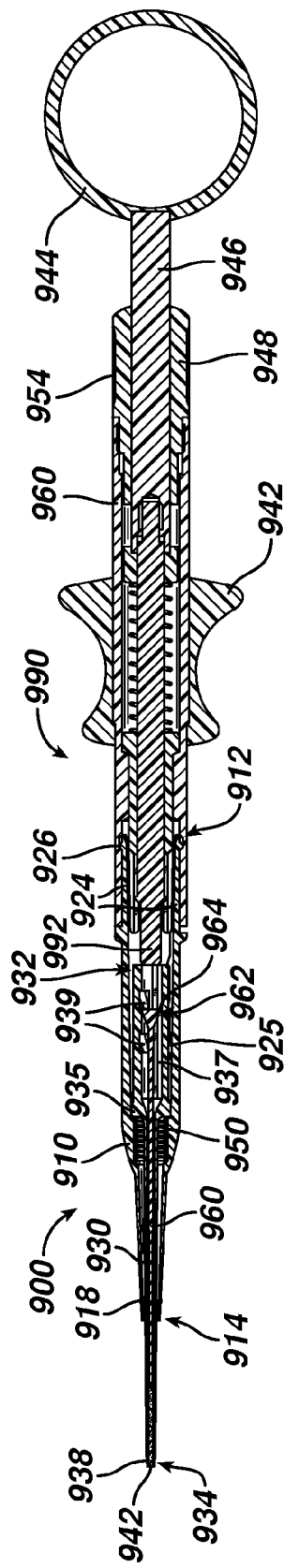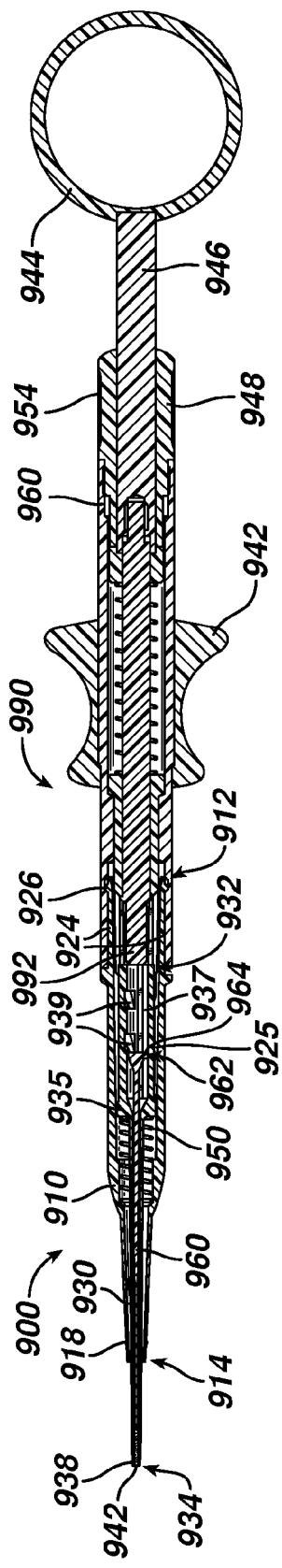

MEDICINAL IMPLANT DEVICE AND CARTRIDGE

This application claims the benefit of U.S. provisional application 61/119,212 filed on Dec. 2, 2008, the complete disclosure of which is hereby incorporated herein by reference for all purposes.

FIELD OF THE INVENTION

The present invention relates to a cartridge for containing a medicament and a device for inserting the medicament in a body cavity of a mammal.

BACKGROUND OF THE INVENTION

Periodontal disease is a general term for a variety of dental conditions associated with either gingivitis or periodontitis. Gingivitis is an inflammation of the gingiva, or gums. It is commonly associated with poor oral hygiene and/or the hormonal state of the patient. If left untreated, gingivitis may develop into periodontitis.

Periodontitis is a bacterial disease in which the infection has progressed to involve the oral tissues that retain the teeth in the jawbone. With this disease the gums become red and inflamed. This condition, if untreated, results in damage to the ligaments and bone holding the teeth in place, and formation of pockets around the teeth. As the pockets become deeper, teeth loosen, to a point where they may fall out. Dental practitioners determine the severity of periodontitis, by measuring the depth of these pockets and reviewing x-rays of the teeth and surrounding bone.

Periodontal disease involves a different treatment protocol than other oral diseases. While many oral diseases can be treated with proper hygiene, fluoride, pastes, washes and rinses, periodontal disease is often resistant to this treatment. This is because of differences between the oral and periodontal cavities. The oral cavity is essentially an aerobic environment, constantly perfused by saliva. In contrast, the periodontal cavity is more anaerobic, and is perfused by plasma filtrate, known as "crevicular fluid". The growth of microorganisms within the periodontal cavity microenvironment may cause periodontal disease. As the disease progresses, the periodontal microenvironment becomes more anaerobic, and the flow of crevicular fluid increases.

Efforts to treat periodontal disease have met with limited degrees of success. This is because the site of the bacterial infections in the periodontal cavity are largely inaccessible to agents present in the oral cavity as well as agents provided to the oral cavity, such as mouthwashes, rinses and the like. Moreover, the increased outflow of crevicular fluid that accompanies periodontal disease inhibits therapeutic agents placed into the oral cavity from entering the pockets.

Oral systemic administration of antibiotics has been shown to be a useful method of controlling subgingival flora in some cases. However, because of side effects, such as those of the digestive system, oral systemic administration has had only limited use in treating periodontal disease. Oral systemic therapy also requires frequent dosing; so patient compliance is frequently a problem.

Recently, efforts have focused on delivering therapeutic agents directly to these pockets, in some cases, in a controlled release formulation. In general, administration of agents directly to the pocket permits higher local drug concentrations that can be safely achieved by systemic administration. Also, some agents such as growth factors must be administered directly to the target site, i.e., the periodontal pocket. Also, as these products are typically administered by dental professionals, patient compliance is not an issue.

Administration of microparticles in dry form to the periodontal pocket by use of an apparatus has been disclosed in U.S. Pat. Nos. 5,236,355, 5,366,733 and 5,622,498, all to Brizzolara, et al., and U.S. Pat. No. 6,682,348, to Lawter, et al., the contents each of which are incorporated by reference herein. These patents disclose treating dental diseases by administration of dry microparticles to the periodontal pocket. Microparticles suitable for this purpose may have compositions, as described in U.S. Pat. Nos. 5,000,886, 5,143,661 and 5,500,228, all to Lawter, et al., all three of these patents are incorporated by reference herein, and U.S. Pat. Nos. 5,236,355, 5,366,733 and 5,622,498, all to Brizzolara, et al., and may be produced by the methods disclosed in the aforementioned six U.S. patents.

The apparatus described in the above listed patents deliver microparticles by use of a plunger to push microparticles out of a hollow cannula. The outlet of the cannula is inserted into a periodontal pocket prior to delivery of the microparticles. During administration of microparticles with such a device, there is a tendency to push the cannula outlet against tissue in the bottom of the periodontal pocket while pushing on the plunger. Tissue may block the outlet and increase the force required to push the microparticles out. At high doses of microparticles in a dry powder form, the force may be too large to easily push out the medicament, since the force required to expel a dry powder will increase rapidly with the length of the powder column. This effect may be overcome to some extent by increasing the interior diameter of the tip. However, when it is desired to deliver microparticles to a body cavity of small dimensions such as a periodontal pocket, there are limitations on the diameter of the tip. Thus, there is a need for improved devices for delivering medicaments to periodontal pockets of a human or animal. There is also a need for a device that provides the ability to administer multiple doses of a medicament.

SUMMARY OF THE INVENTION

The present invention is directed to cartridges for use in a device for inserting a medicament within a body cavity of a mammal, e.g. the periodontal pocket of a human or animal. The cartridge for inserting the medicament includes a housing comprising a proximal portion, a distal portion and a housing slot disposed along a longitudinal axis of the housing. The housing slot has a distal end, a proximal end, a longitudinal axis and a transverse axis. The distal and proximal ends of the housing slots are terminated by protrusions extending across the transverse axis of the slot. The cartridge further includes a retractable chamber disposed within the housing. The retractable chamber comprises a distal internal surface, an external surface and a distal lumen defined by the distal internal surface. The cartridge also comprises a substantially stationary member disposed within the lumen of the retractable chamber. The substantially stationary member has a uniform cross-section sized to provide a sliding fit within the lumen to provide for retraction of the retractable chamber about the substantially stationary member upon actuation of the device. The substantially stationary member comprises a proximal end having a substantially circular cross section and a locking tab located on and extending from the perimeter of the proximal end. The locking tab is in alignment with and disposed within the housing slot. The cartridge also includes a means for retracting the retractable chamber wherein the substantially stationary member is maintained in a substantially stationary position relative to the device and the body cavity.

Depending on the number of doses of medicament contained within the retractable chamber, the housing may comprise a single, or multiple, housing slots. Upon activation of the device, interaction of the substantially stationary member (SSM) locking tab with the housing slot prevents the SSM from moving forward relative to the device when medicament is administered. Upon reset of the device for administration of additional doses of medicament, the SSM locking tab is urged into the next housing slot by the advancing member.

The present invention is also directed to a device for inserting a medicament within a body cavity of a mammal, e.g. the periodontal pocket of a human or animal. The device includes a cartridge for containing medicament, as described above. Medicament may be disposed within the chamber. The chamber may have a distal tip with a uniform external cross-section sized to fit within the body cavity. The device also includes means for activating the means for retracting the retractable chamber. The device thus is configured so that the medicament is expelled from the opening of the chamber by retraction of the chamber about the medicament and the substantially stationary member, rather than by forward movement of the substantially stationary member within the chamber to force the medicament from the end of the barrel.

The device of the present invention is utilized in a method for administering a medicament to body cavity of a mammal, e.g. the periodontal pocket of a human or animal, including: obtaining the medicament containing cartridge and the actuator for dispensing medicament; attaching the cartridge to the actuator; and pressing the operating level or trigger of the actuator to retract the retractable chamber while maintaining the substantially stationary member in a substantially stationary position relative to the device and the body cavity so that the medicament is expelled from the opening of the chamber by refraction of the chamber about the medicament and the substantially stationary member.

BRIEF DESCRIPTION OF THE FIGURES

FIG. 8a is a cross-sectional side view of an exemplary embodiment of the medicament delivery device according to the present invention, prior to delivery of a first dose of the medicament;

FIG. 8b is a cross-sectional side view of the embodiment of FIG. 8a after delivery of the first dose of medicament;

FIG. 8c is a cross-sectional side view of the embodiment of FIG. 8b when reset for delivery of a second dose of medicament;

FIG. 8d is a cross-sectional side view of the embodiment of FIG. 8c after delivery of the second dose of medicament.

DETAILED DESCRIPTION OF THE INVENTION

Figure 1A:
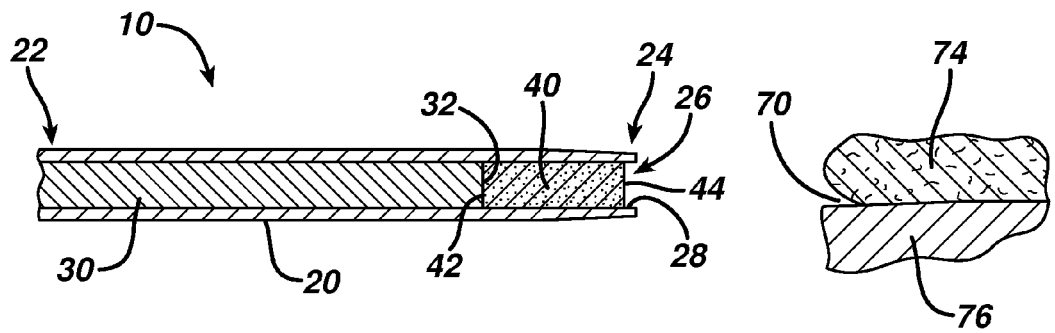
FIG. 1a is a cross-sectional side view of a distal portion of a chamber containing a medicament disposed therein in accordance with one embodiment of the invention, prior to delivery of the medicament into the body of a mammal.
Figure 1B:
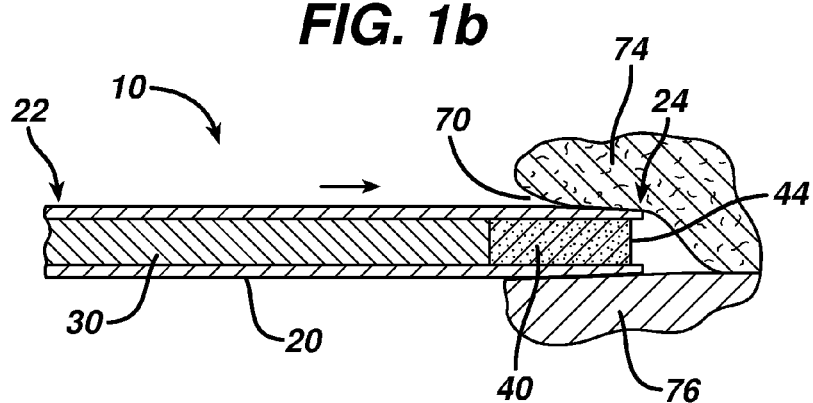
FIG. 1b is a cross-sectional side view of the chamber of FIG. 1a placed at the site of delivery of medicament.
Figure 1C:
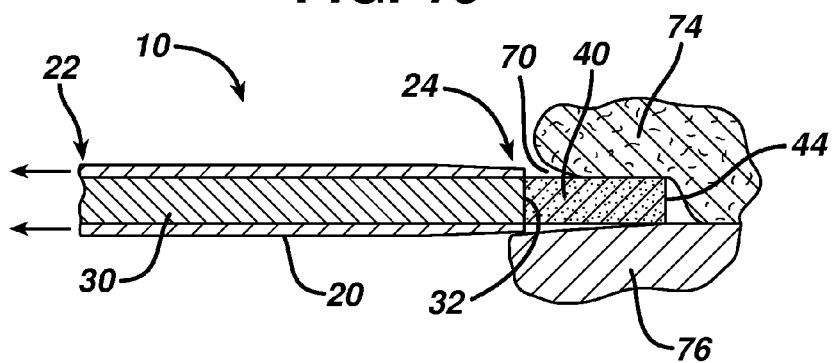
FIG. 1c is a cross-sectional side view of the chamber of FIG. 1b after delivery of medicament at the site of delivery.
Figure 1D:
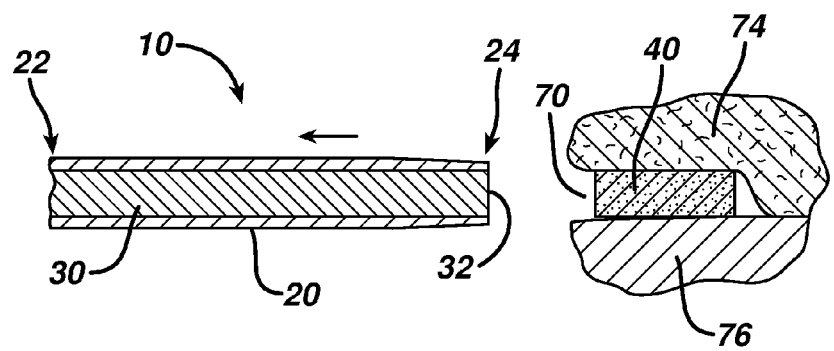
FIG. 1d is a cross-sectional side view of the chamber of FIG. 1c upon removal from the mammal after delivery of medicament to the mammal.

The present invention relates to devices used to administer medicaments into a body cavity of a mammal, e.g. the periodontal pocket of a human or animal. The devices may contain a single dose or multiple doses of medicament, for example in solid powder form, as discussed herein. Such devices include a cartridge for housing a retractable chamber, the retractable chamber for containing medicament, and an actuator for placing the device in operation once the distal portion of the medicament-containing chamber is inserted within the body cavity, thus providing for delivery of the medicament within the body cavity. In certain embodiments, devices may include a sealing means, such as a gasket, to prevent backflow of the medicament between the internal surface of the chamber and the substantially stationary member upon operation of the device. Devices of the present invention are particularly useful and advantageous for administration of a medicament to the periodontal pocket of a mammal for treatment of periodontitis.

In practice, the medicament is placed within the retractable chamber and the chamber then is placed within the cartridge. The cartridge then is connected to the actuator in operational engagement. The distal tip of the retractable chamber extending beyond the distal end of the cartridge is placed within the body cavity at the desired site of delivery of medicament. The actuator then is employed in cooperation with the cartridge to retract the chamber away from the delivery site in a direction towards the actuator. Upon retraction of the chamber, the substantially stationary member (hereinafter SSM) within the chamber that is in contact with the medicament maintains the medicament at the delivery site, thus leaving the medicament that was disposed within the tip of the chamber in the body cavity at the desired delivery site.

Cartridges used in devices of the present invention are replaceable and may include a single or multiple doses of medicament contained therein. Multiple doses are advantageous, as a single cartridge may be employed to deliver medicament to multiple delivery sites prior to replacement. This is particularly advantageous for administration of a medicament to the periodontal pocket of a human for treatment of periodontitis, where delivery at multiple sites often is required and discomfort of the patient may be a substantial issue.

The chamber used in devices according to the present invention, may be in the form of a retractable, cannulated barrel, where the barrel has an outer surface and an inner surface forming the body of the barrel. The lumen of the barrel then is defined by the configuration of the inner surface. Devices also include an SSM disposed within the lumen of the barrel. The respective cross-sections of the lumen of the barrel and the SSM are sized to provide a slidable fit between the inner surface of the barrel and the outer surface of the SSM. By slidable fit, it is meant that co-axial movement of the barrel relative to the SSM may be accomplished without use of excessive force, while maintaining a spatial relationship between the inner surface of the barrel and the outer surface of the SSM, so as to avoid unnecessary movement or "wobbling" of the SSM within the barrel. Upon activation of the device, the barrel slides about the SSM in a lateral direction away from the body cavity, towards the distal end of the device, while the SSM itself remains substantially stationary. By substantially stationary, it is meant that, upon activation of the device to deliver the medicament to the body cavity, the SSM remains in a substantially stationary position in relation to the device itself and to the point within the body cavity at which the medicament is being delivered. While some movement of the SSM relative to the insertion site might occur, any such movement should not be sufficient to cause tissue to block the outlet of the barrel or to appreciably increase the force required to deliver the medicament at the site of insertion. This is particularly advantageous where the medicament may be in the form of a dry solid powder, such as a dry microparticle powder or microspheres.

Typically, but optionally, additives, such as diluents, carriers, excipients, stabilizers or the like may be included in the formulation. In one embodiment, medicaments may be in the form of a particulate composition, such as a dry microparticle powder composition in a sufficient treatment quantity. For example, the composition can be ARESTIN® minocycline Hydrochloride (HCl) microspheres, available from OraPharma, Inc., Warminster, Pa., for example, in a 1 mg dosage, or those compositions as disclosed in U.S. Pat. Nos. 5,000,886, 5,143,661, 5,236,355, 5,366,733, 5,500,228, and 5,622,498, all six disclosures of which are incorporated by reference in their entirety herein. These compositions may comprise matrices of biocompatible and biodegradable polymers, in accordance with the disclosure of U.S. Pat. Nos. 5,236,355, 5,366,733, 5,500,228, and 5,622,498.

For example, dry microparticle compositions may include therapeutic agents, such as antibacterials, antibiotics, antifungal agents, anti-inflammatory agents, immunosuppressive agents, immunostimulatory agents, dentinal desensitizers, odor masking agents, immune reagents, anesthetics, antiseptics, nutritional agents, antioxidants, lipopolysaccharide complexing agents, peroxides, growth factors, or mixtures thereof. The therapeutic agent could also have antibiotic activity.

Exemplary therapeutic agents may be antibiotics such as tetracycline, a pharmaceutically acceptable salt of a tetracycline, hydrates of a tetracycline and hydrates of a pharmaceutically acceptable salt of a tetracycline. The tetracyclines may be doxycycline, a pharmaceutically acceptable salt of doxycycline, hydrates of doxycycline and hydrates of a pharmaceutically acceptable salt of doxycycline. Also, the tetracycline may be minocycline, a pharmaceutically acceptable salt of minocycline, hydrates of minocycline and hydrates of a pharmaceutically acceptable salt of minocycline.

These exemplary therapeutic agents may be present in the form of particles within the medicament. They can typically range from about 0.00001 to about 50 parts by weight per 100 parts by weight of the particles or from about 1 to about 50 parts by weight per 100 parts by weight of the particles, or more particularly from about 4 to about 40 parts by weight per 100 parts by weight of the particles. Alternatively, the therapeutic agent may be present in the medicament as a liquid or gas.

Polymers for the aforementioned matrices may include polyglycolide, poly(l-lactide), poly(dl)lactide, poly(glycolide-co-lactide), poly (glycolide-co-lactide), poly(hydroxybutyric acid, poly(orthoesters), poly(p-dioxanone) and mixtures thereof. The polymers can also be block copolymers of polyglycolide, trimethylene carbonate and polyethylene oxide or polyoxyethylene-polyoxypropylene copolymers. The polymers can also be biopolymers and their derivatives including cellulose, cellulose derivatives (oxidized regenerated cellulose), starch, gelatin, chitosan, and hyaluronan. These polymers may also be such that they become tacky upon contact with water.

The aforementioned particles of particulate compositions including therapeutic agents may, for example, have particles with diameters ranging from about 0.1 to about 1,000 microns, or from about 10 to about 200 microns, or from about 20 to about 120 microns.

While the figures are presented as exemplary embodiments of the inventions, they are not intended to limit the scope of the invention or the claims appended hereto. Use of the same reference symbols in different figures indicates similar or identical items.

One embodiment of the present invention is shown in FIG. 1a. FIG. 1a is a cross-sectional side view of a distal portion of retractable chamber 10, in the form of retractable barrel 20 for holding a dose of medicament 40. Medicament 40 is disposed in the lumen defined by the internal surface 28 of barrel 20. Substantially stationary member (SSM) 30 is disposed within barrel 20. Barrel 20 is cannulated to allow passage co-axially about SSM 30, and has proximal 22 and distal 24 ends, as well as a distal opening 26. SSM 30 is shown to have distal face 32. Medicament 40 is located in cannulated barrel 20, and has proximal 42 and distal 44 interfaces. The proximal interface 42 is in contact with distal face 32 of SSM 30. The cross-sectional dimensions, e.g. the diameter, of the lumen of barrel 20 relative to the cross-sectional dimension of SSM 30 is such that barrel 20 may move co-axially about SSM 30 in a sliding fit without medicament 40 leaking between SSM 30 and inner surface 28 of barrel 20, and provide for retraction of barrel 20 around SSM 30. This is particularly applicable to medicaments in powder form. The cross-sectional shape of SSM 30 and lumen of barrel 20 may be hexagonal, octagonal, elliptical or any other shape, with a circular cross-sectional shape being preferred. In one embodiment, SSM 30 has a bell shaped feature (not shown) on the both ends to create seals with barrel 20.

Suitable materials from which barrel 20 and SSM 30 may be formed include glasses, non-corrodible metals, synthetic resins such as plastics, and the like. These materials may be used alone or in combination. If the device components are made of glasses, non-corrodible metals, or sterilizable synthetic resins, they may be used repeatedly by performing sterilization. Preferably, barrel 20 and SSM 30 are formed from synthetic resins such as plastics. Plastics may include polyethylene, polypropylene, and polycarbonate.

FIGS. 1a to 1d show the steps in the delivery of medicament 40 to a delivery site 70 of a patient. In this embodiment, delivery site 70 is in the form of a pocket between a first tissue 74, for example a gum, and a second tissue 76, for example a tooth, such as a periodontal pocket in a mammal. FIG. 1a show chamber 10 prior to delivery, where proximal interface 42 of medicament 40 is in contact with distal face 32 of SSM 30. In the first step, chamber 10 is placed at delivery site 70 by inserting distal end 24 in the direction of the arrow in FIG. 1b into site 70. Now, SSM 30 is held substantially stationary while barrel 20 is retracted about SSM 30 in the direction of the arrow in FIG. 1c. Medicament 40 is delivered from the barrel distal opening 26 by retracting barrel 20. Medicament 40 is fully administered when distal end 24 of barrel 20 reaches distal face 32 of SSM 30. Finally, chamber 10 is removed from delivery site 70 (see FIG. 1d) in a distal to proximal direction, leaving medicament 40 at delivery site 70.

Figure 2A:
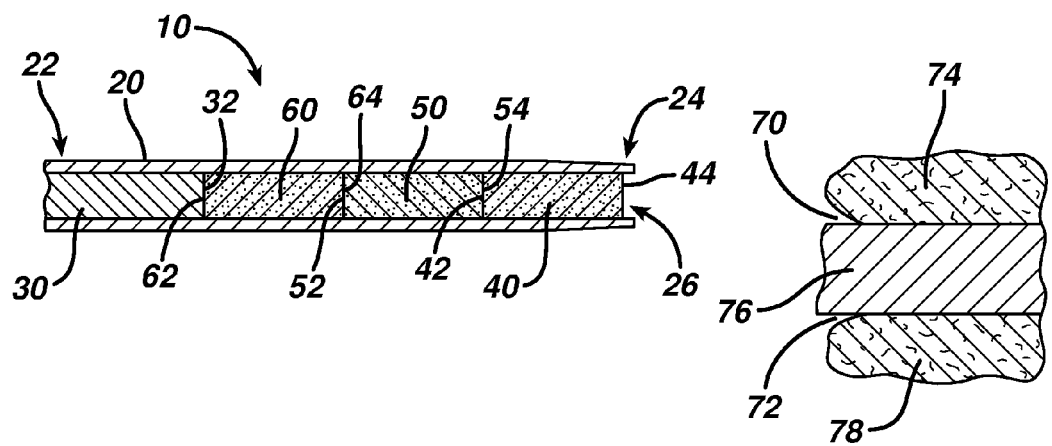
FIG. 2a is a cross-sectional side view of a distal portion of a chamber containing multiple doses of a medicament disposed therein in accordance with one embodiment of the invention, prior to delivery of the medicament into the body of a mammal.
Figure 2B:
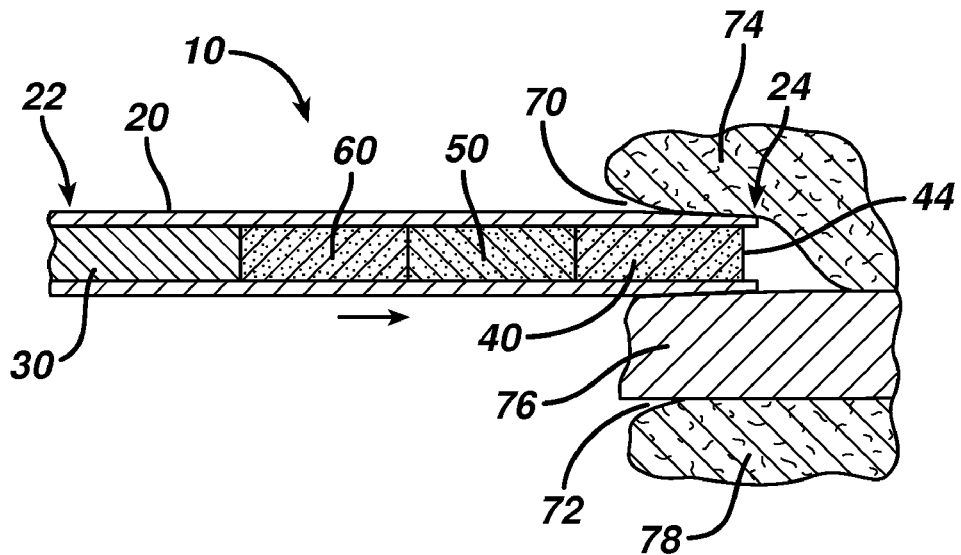
FIG. 2b is a cross-sectional side view of the chamber of FIG. 2a placed at the site of delivery of the first dose of medicament.
Figure 2C:
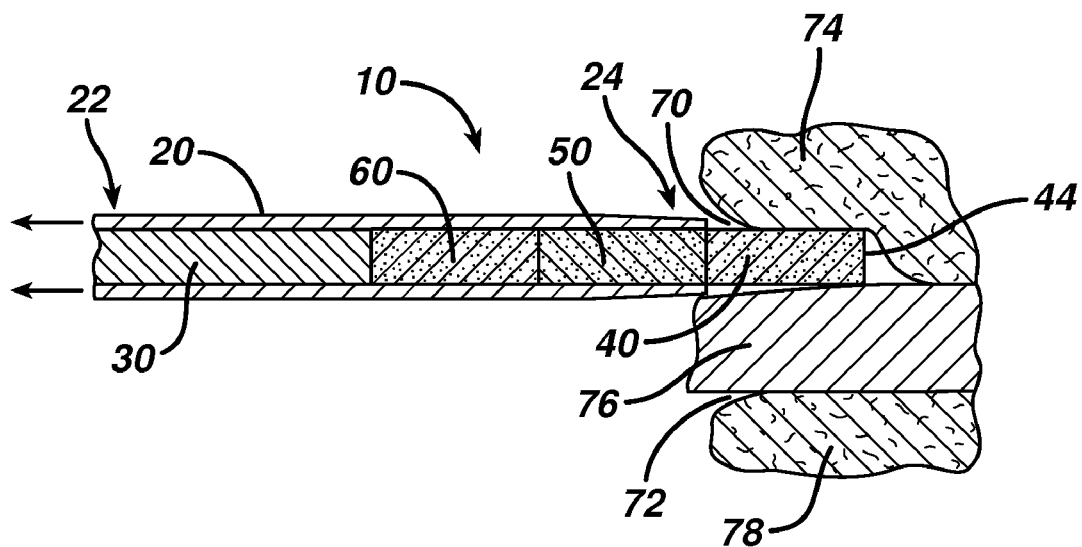
FIG. 2c is a cross-sectional side view of the chamber of FIG. 2b after delivery of the first dose of medicament to the mammal.
Figure 2D:
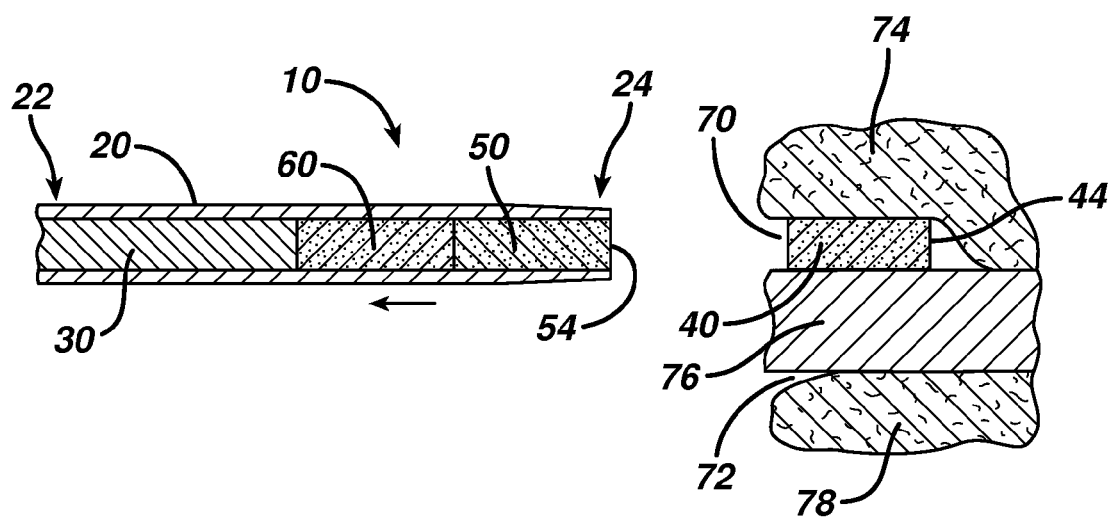
FIG. 2d is a cross-sectional side view of the chamber of FIG. 2c upon removal from the mammal after delivery of the first dose of medicament to the mammal.
Figure 2E:
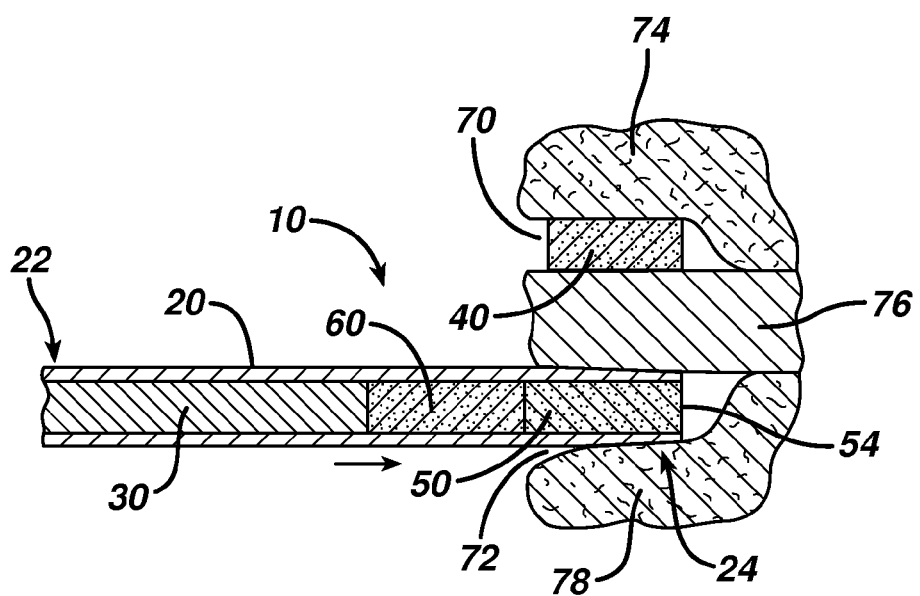
FIG. 2e is a cross-sectional side view of the chamber of FIG. 2d placed at the site of delivery of the second dose of medicament.
Figure 2F:
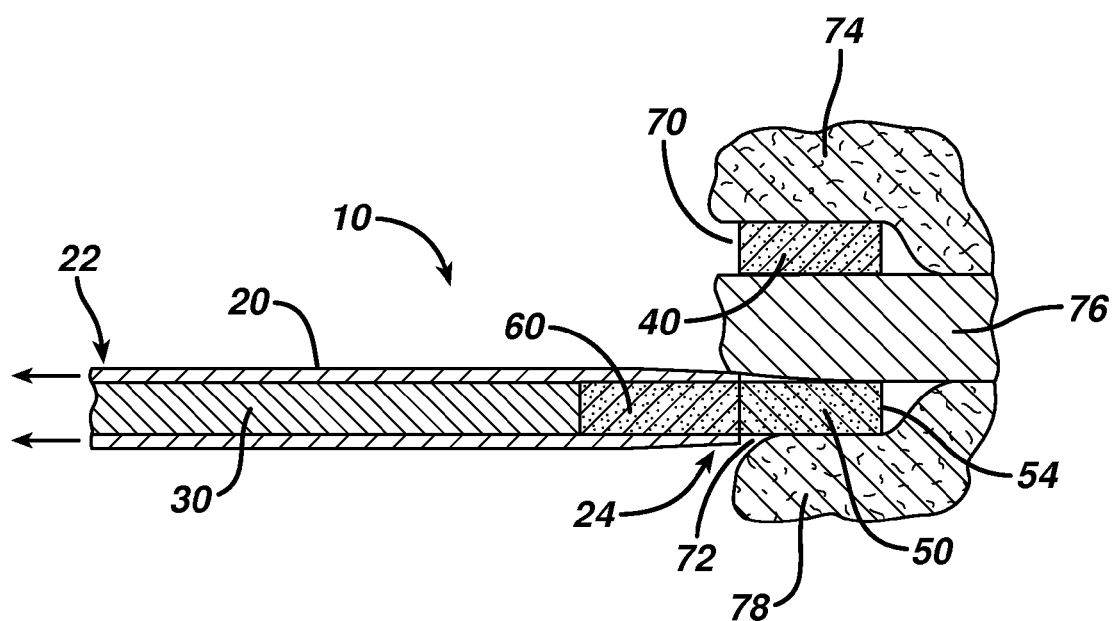
FIG. 2f is a cross-sectional side view of the chamber of FIG. 2e after delivery of the second dose of medicament to the mammal.

An alternative embodiment of the present invention is shown in FIG. 2a. FIG. 2a is similar to FIG. 1a, except that multiple doses 40, 50, and 60 are located in the lumen (defined by the internal surface of barrel 20) of retractable barrel 20. Additional doses of medicament may be disposed within barrel 20, for example four or more doses. Second medicament dose 50 has proximal 52 and distal 54 interfaces. Third medicament dose 60 has proximal 62 and distal 64 interfaces. Second and third medicament doses 50 and 60 may be comprised of the same formulation as first medicament dose 40, or of a different formulation than first medicament dose 40. The embodiment as shown in FIG. 2a allows for the delivery of multiple doses of medicament.

FIGS. 2a to 2f show the steps in the delivery of medicament doses 40 and 50 to first delivery site 70 and second delivery site 72, respectively. In this embodiment, first delivery site 70 is in the form of a pocket between a first tissue 74 and a second tissue 76, while second delivery site 72 is in the form of a pocket between a second tissue 76 and a third tissue 78. First delivery site 70 and second delivery site 72 may be, for example periodontal pockets in a mammal. FIG. 2a shows chamber 10 prior to delivery, where proximal interface 42 of first medicament dose 40 is in contact with distal interface 54 of second medicament dose 50 and proximal face 52 of second medicament dose 50 is in contact with distal face 64 of third medicament dose 60. In the first step, chamber 10 is placed at delivery site 70 (see FIG. 2b). Now, SSM 30 is held substantially stationary while barrel 20 is retracted in the direction of the arrow in FIG. 2c. First medicament dose 40 is delivered from the barrel distal opening 26 by retracting barrel 20. First medicament dose 40 is fully administered when distal face 54 of second medicament dose 50 reaches distal end 24 of barrel 20. Next, chamber 10 is removed from delivery site 70 (see FIG. 2d) from a distal to proximal direction, leaving first medicament dose 40 at delivery site 70. Next, chamber 10 is aligned for next delivery and then placed at delivery site 72 (see FIG. 2e). Now, SSM 30 is held substantially stationary while barrel 20 is retracted in the direction of the arrow in FIG. 2f. Second medicament dose 50 is delivered from the barrel distal opening 26 by retracting barrel 20. Second medicament dose 50 is fully administered when proximal face 52 of second medicament dose 50 reaches distal end 24 of barrel 20. Next, chamber 10 is removed from delivery site 72 from a distal to proximal direction, leaving second medicament dose 50 at delivery site 72. This process may be repeated depending on the desired number of doses of medicament to be administered.

Figure 3:
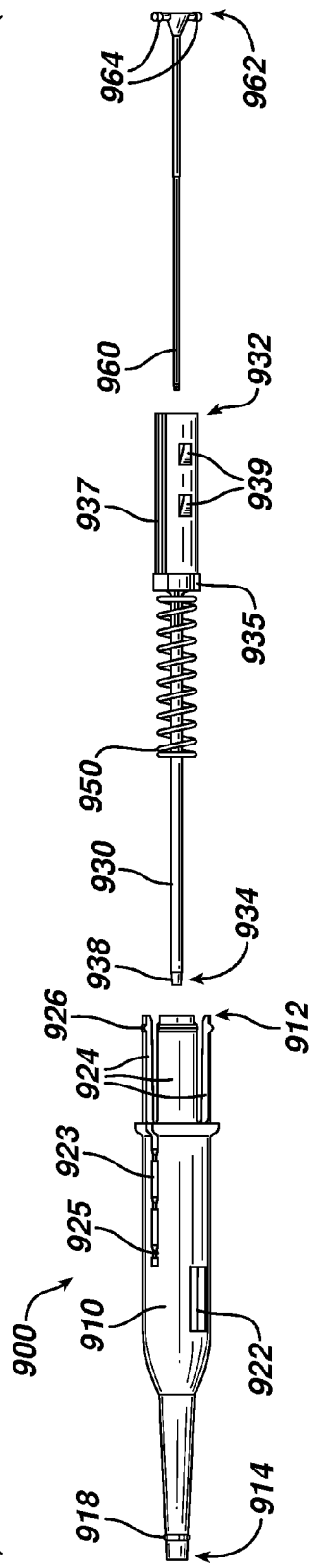
FIG. 3 is an exploded view of a cartridge in accordance with one embodiment of the invention.

FIG. 3 is an exploded view of a cartridge in accordance with one embodiment of the invention. Such cartridges will include disposed therein a retractable chamber for retaining medicament, means for retracting the chamber, and a substantially stationary member (SSM) disposed within the chamber. Components of cartridge 900 include housing 910, barrel 930, cartridge spring 950 disposed about barrel 930 for enabling barrel 930 to retract upon actuation of the device, and substantially stationary member (SSM) 960 disposed within barrel 930. All components of cartridge 900 may be made from stainless steel or known plastics, or, optionally, any material that can be sterilized. Barrel 930 may optionally contain a lubricant to facilitate delivery of the medicament. The lubricant may be applied to the surfaces of the barrel or may be included as a slip agent in a resin used to manufacture the part by injection molding.

In the embodiment now presented, up to three doses of medicament may be delivered to a body cavity of a mammal. However, cartridge 900 may be modified so as to be capable of delivering one or more, for example three or more doses to a body cavity of a mammal.

Barrel 930 includes proximal end 932 and distal end 934, barrel extension 935, barrel slot 937, distal tip 938, and means for advancing SSM 960 when barrel 930 is advanced, such as advancing members 939 extending from the internal surface of the barrel. Such advancing members may be, for example, tabs, protrusions, or the like, which are in contact and interact with proximal end 962 of SSM 960 to advance SSM 960 during reset of the device between administration of successive doses.

Housing 910 may be made from the same materials as barrel 930. Housing 910 includes proximal end 912 and tapered distal end 914. Though not shown, distal end 914 of housing 910 may have a bend of approximately 50 degrees to facilitate entry of distal tip 938 of barrel 930 into the body cavity. In such cases, barrel 930 will be made from a plastic and will be flexible so as to traverse the housing. Housing 910 includes at least one housing slot 923 disposed along a longitudinal axis of the housing. Housing slot 923 has a distal end, a proximal end, a longitudinal axis and a transverse axis. Distal and proximal ends of housing slots 923 are terminated by housing slot protrusions 925 which extend across the transverse axis of housing slot 923. FIG. 3 shows multiple housing slots 923, although only one is specifically labeled. Housing 910 may include means for finger gripping which enable the barrel to be rotated. Housing 910 may contain means for retaining a cap to protect the medicament from contamination, such as snap ring 918 located on distal end 914. Housing 910 may include means for limiting the motion of barrel 930, such as slots 922 that align with barrel extension 935. Proximal end 912 of housing 910 may include means for attaching cartridge 900 to an actuator (not shown), such as fingers 924 with flanges 926, which engage an undercut on the tip of the actuator.

Figure 4:
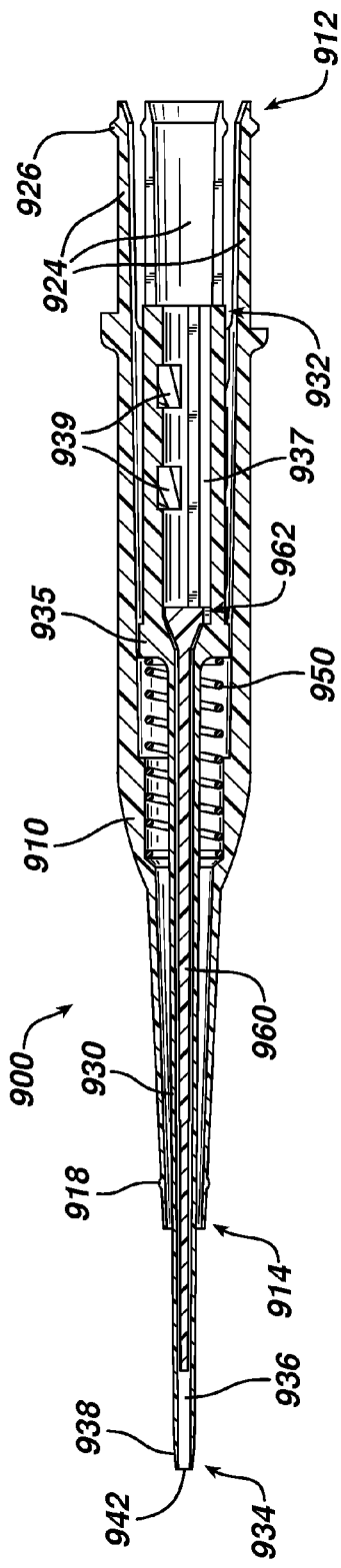
FIG. 4 is a cross-sectional side view of the cartridge of FIG. 3 after assembly.

SSM 960, disposed within cannulation 936 of barrel 930, is sized to provide a sliding fit within cannulation 936 suitable to provide for retraction of the barrel 930 about the member upon actuation of the device. SSM 960 has proximal end 962 having a substantially circular cross section. Proximal end 962 of SSM 960 includes locking tabs 964 located on the perimeter of and extending therefrom. Locking tabs 964 are in alignment with and disposed within housing slot 923 upon use of the device and serve, in concert with housing slots 923, to maintain SSM 960 substantially stationary relative to housing 910 while barrel 930 is retracted. A cross-sectional side view of cartridge 900 useful in the present invention is shown in FIG. 4. As shown, cartridge 900 includes housing 910, barrel 930 disposed within housing 910, cartridge spring 950 disposed about barrel 930 for enabling barrel 930 to retract upon actuation of the device and substantially stationary member (SSM) 960 disposed within barrel 930. Barrel 930 is sized to fit slidably within housing 910. Medicament (not shown in FIG. 3 or 4) is located in cannulation 936 of barrel 930. Distal end 934 of barrel 930 includes distal tip 938 and distal opening 942. Cartridge spring 950 biases barrel 930 towards proximal end 912 of housing 910 to provide a retracting motion for barrel 930 when actuated. Barrel slot 937 is aligned with housing slot 923, and locking tabs 964 are disposed there through.

Figure 5:
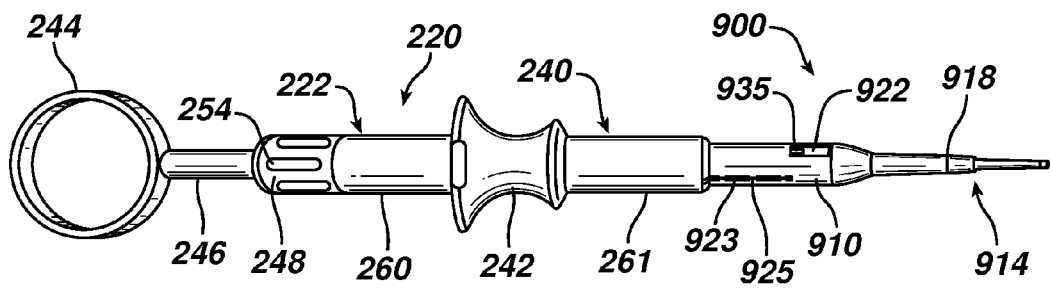
FIG. 5 is side view of the apparatus disclosed herein.

Dispensing medicament from cartridge 900 of the present invention is effected by an actuator used in operational engagement with the cartridge. FIG. 5 is side view of an exemplary embodiment of the medicament delivery device according to the present invention. The figure shows a device comprised of cartridge 900 (as described in FIGS. 3 and 4) and actuator 220. Actuator 220 has been described in U.S. Pat. No. 6,682,348, to Lawter, et al., the contents of which are incorporated by reference herein.

FIG. 5 shows a device formed from an actuator 220 and a cartridge 900 that connects to the actuator 220 and is separable therefrom. Though not shown, the end of cartridge 900 is typically covered by a cap or other closing member, typically in a frictional engagement, which maintains the integrity of the composition in the cartridge 900 until actual use, when this cap is removed.

Actuator 220 is of a configuration and dimensions similar to other dental instrumentation. Actuator 220 is formed of a sleeve 240, with a fingergrip 242 surrounding it. A thumb ring 244, connected to a spring loaded shaft 246, extends from the sleeve 240, with the shaft 246 held in place by a nut member 248, that includes a threaded portion 250 (FIG. 7) that connects to a correspondingly threaded portion 251 (FIG. 6) on the inner wall 252 (FIG. 6) of the sleeve 240. The nut member 248, on a proximal portion 248*a* (FIG. 7), includes a roughened, knurled or grooved outer surface 254, to assist the user in gripping, when opening actuator 220 is desired.

Figure 6:
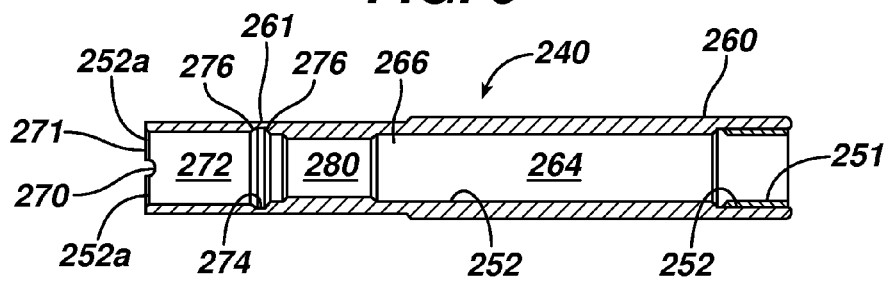
FIG. 6 is a cross sectional view of the sleeve of FIG. 5 with the finger rest removed.
Figure 7:
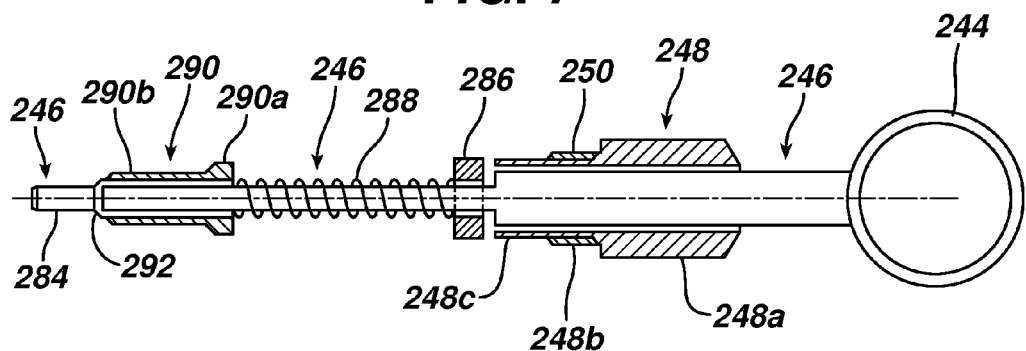
FIG. 7 is a cross-sectional view of the shaft and associated components of FIG. 5.

Turning also to FIGS. 6 and 7, actuator 220 is separated into the sleeve 240 (FIG. 6) and the shaft 246 and associated components (FIG. 7). The sleeve 240 includes a proximal end 260 and a distal end 261. The proximal end 260 includes a correspondingly threaded portion 251 along its inner wall 252, for accommodating the threaded portion 250 on an intermediate 248*b* portion of the nut member 248. Moving distally (in a direction away from the thumb ring 244), there is a spring section 264 for accommodating the spring 288 and its proximal confinement 286 and distal confinement 290, specifically its head 290*a*. This spring section 264 chamber includes a reduced diameter portion 266, that serves as a stop surface for the head 290*a* of the distal confinement 290, when the shaft 246 is pushed distally by the thumb ring 244.

The distal end 261 includes a notch (or indent) 270 at the outer edge 271 of the sleeve 240, for receiving a corresponding nub on the cartridge 900, to prevent the cartridge 900 from rotating in the sleeve 240 (of actuator 220) when the cartridge 900 (in particular, its flanges 926, see FIG. 3) is locked in place in actuator 220, as detailed below. Proximal of this notch 270 is a chamber 272 for accommodating the flanges 926 of cartridge 900 as pushed outward by the body 290*b* of the distal confinement 290. The chamber 272 terminates at a groove 274 that typically extends continuously around the inner wall 252 of the sleeve 240. The groove 274 is typically triangular in its edges 276, to accommodate the corresponding flanges 926 (FIG. 3) on the fingers 924 (FIG. 3) of cartridge 900, upon their seating therein, when cartridge 900 is locked in actuator 220.

These triangular edges 276 allow for removal of cartridge 900 from actuator 220, as the flanges 926 of the fingers 924 can slide over these edges 276, allowing for the release of cartridge 900. A section 280 for accommodating the body 290*b* of the distal confinement 290 is intermediate the groove 274 and the spring section 264.

The shaft 246 extends (in the distal direction) from the thumb ring 244 to the shaft end 284 (distal end). The nut member 248, proximal confinement 286, spring 288 and distal confinement 290 (formed of a head 290*a* and a body 290*b*) are all torroidal and slideable on the shaft 246. When the nut member 248 is attached to the sleeve 240 (so as to be fixed), in its normal operation, the nut member 248, at its distal portion 248*c*, serves as a confinement for the proximal confinement 286, when the shaft 246, typically via the thumb ring 244, is moved in the proximal direction (outwards with respect to the sleeve 240). The shaft 246 includes an outwardly extending ring 292 at its distal end 284. This ring 292, typically molded as part of the shaft 246, is fixed, and serves to limit distal movement of the distal confinement 290 for the spring 288.

Actuator 220 and all components thereof, except the spring 288, is typically made of materials such as metals and in particular surgical grade steels, for example, 303 Stainless Steel. The spring 288 is typically made of metals such as surgical grade steels, and for example, stainless steels other then 303 Stainless Steel. Accordingly, actuator 220, including the spring 288, is sterilizable and reusable. Actuator components may also be made by injection molding of suitable resins.

Figure 8E:
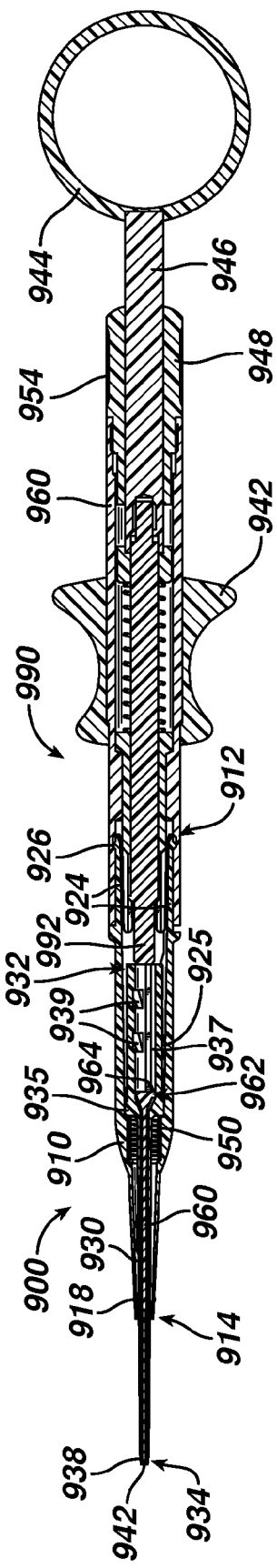
FIG. 8e is a cross-sectional side view of the embodiment of FIG. 8d when reset for delivery of a third dose of medicament.

FIG. 8*a* shows an exemplary embodiment of the medicament delivery device prior to delivery of a first dose of the medicament. As shown in FIG. 8*a*, cartridge spring 950 is in a compressed state and shaft 946 of actuator 990 is engaged with the proximal end 932 of barrel 930. Cartridge spring 950 is held in a compressed state by a proximal-to-distal force on shaft 946, creating a bias for moving barrel 930 towards the proximal end 912 of housing 910. Locking tabs 964 are engaged with housing slots bounded by first housing slot protrusion 925, which maintains SSM 960 stationary relative to housing 910 while barrel 930 is retracted.

To deliver a first dose of medicament, the proximal-to-distal force on shaft 946 is released. As shown in FIG. 8*b*, cartridge spring 950 now elongates, moving barrel 930 towards proximal end 912 of housing 910. Since tabs 964 of SSM 960 are engaged with housing slots and housing slot/protrusions 925, SSM 960 remains in a relative stationary position with respect to barrel 930 as barrel 930 moves towards proximal end 912 of housing 910. The retracting motion of barrel 930 releases medicament from distal opening 942 of barrel 930, delivering the first dose of medicament to the delivery site. Proximal end 962 of SSM 960 is engaged with first stop of advancing member 939.

To reset device for delivery of a second dose of medicament, user exerts proximal-to-distal force on shaft 946. Shaft 946, engaged with proximal end 932 of barrel 930, moves towards the distal end 914 of housing 910, compressing cartridge spring 950. Likewise, SSM 960, engaged with advancing member 939, moves towards the distal end 914 of housing 910, thereby moving locking tabs 964 into second housing slots as shown in FIG. 3. Cartridge spring 950 is compressed, creating a bias for moving barrel 930 towards the proximal end 912 of housing 910.

FIG. 8*c* shows an exemplary embodiment of the medicament delivery device prior to delivery of a second dose of the medicament. As shown in FIG. 8*c*, cartridge spring 950 is in a compressed state and shaft 946 of actuator 990 is engaged with the proximal end 932 of barrel 930. Cartridge spring 950 is held in a compressed state by a proximal-to-distal force on shaft 946, creating a bias for moving barrel 930 towards the proximal end 912 of housing 910. Tabs 964 are engaged with second housing slots and housing protrusion 925, which keeps SSM 960 stationary relative to housing 910 while barrel 930 is retracted.

To deliver a second dose of medicament, the proximal-to-distal force on shaft 946 is released. As shown in FIG. 8d, cartridge spring 950 now elongates, moving barrel 930 towards proximal end 912 of housing 910. Since tabs 964 of SSM 960 are engaged with housing slot protrusions 925, SSM 960 remains in a relative stationary position with respect to barrel 930 as barrel 930 moves towards proximal end 912 of housing 910. The retracting motion of barrel 930 releases medicament from distal opening 942 of barrel 930, delivering the first dose of medicament to the delivery site. Proximal end 962 of SSM 960 is engaged with second stop of advancing member 939.

The process can be repeated for delivery of a third dose of medicament.

In the embodiments presented above, up to three doses of medicament may be delivered to a body cavity of a mammal. However, cartridge 900, may be modified so as to be capable of delivering one or more, for example three or more doses to a body cavity of a mammal.

We claim:

1. A device for inserting a medicament within a body cavity of a mammal, said device comprising:
   a cartridge for containing said medicament therein, said cartridge comprising,
      a housing comprising a proximal portion, a distal portion and a housing slot disposed along a longitudinal axis of said housing, said housing slot having a distal end, a proximal end, a longitudinal axis and a transverse axis, wherein said distal and proximal ends are terminated by housing slot protrusions extending across said transverse axis of said housing slot,
      a retractable chamber disposed within said housing, said retractable chamber comprising a distal internal surface, an external surface and a distal lumen defined by said distal internal surface,
      a substantially stationary member disposed within said lumen of said retractable chamber and having a uniform cross-section sized to provide a sliding fit within said lumen to provide for retraction of said retractable chamber about said substantially stationary member upon actuation of said device, said substantially stationary member comprising a proximal end having a substantially circular cross section and a locking tab located on the perimeter of said proximal end in alignment with and disposed within said housing slot; and
      means for retracting said retractable chamber about said substantially stationary member; and
   means for activating said means for retracting said retractable chamber,
   wherein said locking tab disposed within said housing slot maintains said substantially stationary member in a substantially stationary position upon actuation of said device.

2. The device of claim 1 comprising a plurality of housing slots.

3. The device of claim 1 wherein said means for retracting said retractable chamber about said substantially member comprises a spring disposed about said retractable chamber.

4. The device of claim 2 wherein said retractable chamber further comprises an advancing member for advancing said substantially stationary member, said advancing member extending from an internal surface of said retractable chamber.

5. The device of claim 1 comprising a medicament disposed within said cartridge.

6. The device of claim 5 wherein said dry microparticle powder comprises a medicament selected from the group consisting of a tetracycline, a pharmaceutically acceptable salt of a tetracycline, hydrates of a tetracycline and hydrates of a pharmaceutically acceptable salt of a tetracycline.

7. A cartridge for use in a device for inserting a medicament within a cavity of a mammal, said cartridge comprising:
   a housing comprising a proximal portion, a distal portion and a housing slot disposed along a longitudinal axis of said housing, said housing slot having a distal end, a proximal end, a longitudinal axis and a transverse axis, wherein said distal and proximal ends are terminated by protrusions,
   a retractable chamber disposed within said housing, said retractable chamber comprising a distal internal surface, an external surface and a distal lumen defined by said distal internal surface,
   a substantially stationary member disposed within said lumen of said retractable chamber and having a uniform cross-section sized to provide a sliding fit within said lumen to provide for retraction of said retractable chamber about said substantially stationary member upon actuation of said device, said substantially stationary member comprising a proximal end having a substantially circular cross section and a locking tab located on the perimeter of said proximal end in alignment with and disposed within said housing slot; and
   means for retracting said retractable chamber about said substantially stationary member,
   wherein said locking tab disposed within said housing slot maintains said substantially stationary member in a substantially stationary position upon actuation of said device.

8. The cartridge of claim 7 comprising a plurality of housing slots.

9. The cartridge of claim 7 wherein said means for retracting said retractable chamber about said substantially member comprises a spring disposed about said retractable chamber.

10. The cartridge of claim 8 wherein said retractable chamber further comprises an advancing member for advancing said substantially stationary member, said advancing member extending from an internal surface of said retractable chamber.

11. The cartridge of claim 7 comprising a medicament disposed within said cartridge.

12. The cartridge of claim 11 wherein said dry microparticle powder comprises a medicament selected from the group consisting of a tetracycline, a pharmaceutically acceptable salt of a tetracycline, hydrates of a tetracycline and hydrates of a pharmaceutically acceptable salt of a tetracycline.

* * * * *